(12) United States Patent
Vilsmeier et al.

(10) Patent No.: US 6,611,700 B1
(45) Date of Patent: Aug. 26, 2003

(54) METHOD AND APPARATUS FOR POSITIONING A BODY FOR RADIATION USING A POSITION SENSOR

(75) Inventors: Stefan Vilsmeier, Poing (DE); Stephan Fröhlich, Aschheim (DE)

(73) Assignee: BrainLAB AG, Kirchheim/Heimstetten (DE)

( * ) Notice: Subject to any disclaimer, the term of this patent is extended or adjusted under 35 U.S.C. 154(b) by 0 days.

(21) Appl. No.: 09/475,701

(22) Filed: Dec. 30, 1999

(51) Int. Cl.$^7$ ................................................ A61B 5/00
(52) U.S. Cl. ........................ 600/407; 600/424; 600/426; 600/427
(58) Field of Search ........................ 600/407, 426, 600/427, 478, 424, 476; 378/65

(56) References Cited

U.S. PATENT DOCUMENTS

| | | | | |
|---|---|---|---|---|
| 5,782,771 A | * | 7/1998 | Hussman | 600/478 |
| 5,866,914 A | * | 2/1999 | Jones | 250/505.1 |
| 6,336,904 B1 | * | 1/2002 | Nikolchev | 600/562 |
| 6,405,072 B1 | * | 6/2002 | Cosman | 600/426 |

FOREIGN PATENT DOCUMENTS

| | | |
|---|---|---|
| DE | 197 50 698 | 5/1998 |
| DE | 198 25 999 | 12/1999 |
| DE | 198 44 767 | 4/2000 |

\* cited by examiner

*Primary Examiner*—Ruth S. Smith
(74) *Attorney, Agent, or Firm*—Renner, Otto, Boiselle & Sklar, LLP

(57) ABSTRACT

The present invention relates to a method for positioning a body (1) for radiation comprising the steps: inserting a position sensor (6) into the body (1); detecting the position of the sensor (6) relative to a point or volume (2) to be irradiated, and positioning the body (1) using signals sensed by the position sensor (6) so that the point or volume (2) to be irradiated is located in a specific site circumscribing an isocenter (3). It also relates to an apparatus for positioning a body (1) including a position sensor (6), which may be placed into the body (1); a controllable patient bench (9) for moving the body (1); a controller (8) which controls the controllable patient bench (9) for moving the body (1) depending on the signals sensed by the position sensor (6).

17 Claims, 2 Drawing Sheets

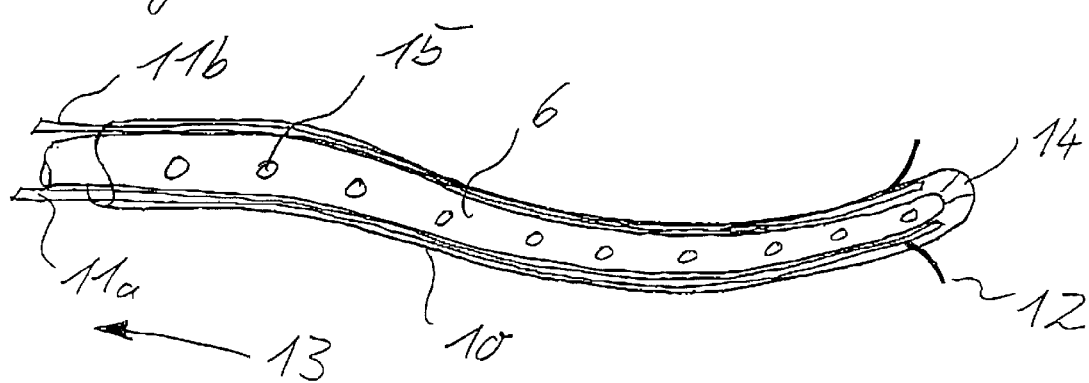

METHOD AND APPARATUS FOR POSITIONING A BODY FOR RADIATION USING A POSITION SENSOR

BACKGROUND OF THE INVENTION

1. Technical Field

The present invention relates to a method for positioning a body to carry out radiation as well as to an apparatus with which such a positioning can be effectuated, the invention also relating to the use of a position sensor in radiosurgery and radiotherapy.

2. Description of Related Art

Radiation finds application in particular in the treatment of tumors in the human body. This involves the use of very high radiation doses, e.g. in radiosurgery, so that a precise positioning of the tissue to be irradiated is vital to preventing destroying surrounding healthy tissue.

Up until now, the location of a tumor is detected e.g. by a computer tomograph of the body, after which fiducial or marker points are applied to the skin surface of the patient to be irradiated. For positioning, the location of the tumor is determined exclusively by the markers applied to the surface of the body, after which radiation is performed. In this arrangement, the tumor of the patient is required to be located in the isocenter e.g. of a linear accelerator for radiation. The term isocenter defines the point in space through which all rays of the linear accelerator pass, irrespective of the location of a table resting the patient, and the gantry angle. When irradiation is carried out from several directions the dose accumulates in the isocenter, the tissue located further away from the isocenter receiving a smaller dose of radiation.

However, using markers arranged on the skin surface to determine the location of the tumor involves problems. For instance, markers attached to the skin surface of the patient to be irradiated may shift out of place so that an incorrect positioning of the isocenter is caused outside of a tumor to be irradiated. The location of the tumor itself may also shift after the markers have been positioned, when e.g. the patient has an a stomach tumor and drinks something after positioning of the markers and prior to irradiation, resulting in the stomach being dilated. In the case of lung tumors, the location of a tumor may be shifted out of place by as much as 2 centimeters due to respiration. These examples make it clear that after the location of a tumor has been detected, e.g. by a computer tomograph, the tissue to be irradiated or the markers may move out of place so that, incorrectly, the isocenter no longer lies in the tissue to be irradiated. This results in healthy tissue being irradiated and destroyed, and the tissue to be irradiated being located only in the border region of the radiation beam or even being no longer exposed thereto.

SUMMARY OF THE INVENTION

An object of the invention is to propose a method and an apparatus for positioning a body for radiation with which a point or site to be irradiated is may be precisely positioned in or surrounding the isocenter so that radiation can be performed which is exact and right on target.

This object is achieved by a method and an apparatus comprising the features of the independent claims. Advantageous embodiments read from the sub-claims.

The advantages to be gained from the invention are based on a position sensor being inserted in the site of a position in the body to be irradiated and the detection of the location of the sensor relative to the point or volume to be irradiated, the body then being positioned using the signals of the position sensor so that the point or site to be irradiated is located in the isocenter or in a pre-given area surrounding it. Actual radiation is then carried out using the position of the tumor determined by the position sensor. A position sensor inserted in the body and positioned relatively shift-proof relative to the site to be irradiated, such as e.g. a tumor, may be anchored e.g. directly in a tumor or in a defined position relative thereto so that any movement of the position sensor relative to the tumor due to e.g. respiration of the patient is now no longer possible. In this arrangement, the position sensor is able to output signals indicating its position from which its three-dimensional location can be definitely determined which can serve to precisely position the body or also to control the radiation beam. In principle, any sensor may be used as the position sensor enabling the three-dimensional location, i.e. for example, the coordinates of a specific point of the sensor in space to be clearly determined. Flexible cable or tape-type sensors are available with the aid of which it is possible to detect the run of the sensor cable three-dimensionally on the basis of the signals output by the sensor. Thus, e.g. the curvature of the sensor at any desired point along its contour may be detected so that one or more fiducial points on the sensor can be easily detected which can be brought into a position relative to a tissue to be irradiated which does not shift out of place or only negligibly so. Once such a position sensor has been inserted in the body in the target site to be irradiated and suitably positioned, precise irradiation of the desired location can be performed using the position signals of the sensor which, preferably, are capable of detecting the precise position of the tissue to be irradiated at any point in time.

Preferably, the position sensor is inserted into the body with the aid of the information obtained from a computer tomograph or nuclear spin tomograph or some other diagnostic examination, such as e.g. palpation, and its end or a defined point on the sensor is positioned in the vicinity of the tumor. Subsequently, the position sensor may be firmly anchored or fixed in place e.g. in the tumor or in the tissue bordering the tumor or in or on a bone. This may be done e.g. by means of supporting or clamping elements externally movable at the inserted position sensor. Afterwards, the location of the position sensor relative to the target point in the target volume, e.g. spacing and directional vector, is determined by means of a suitable technique, e.g. with a second computer tomograph, thus enabling the location of the position sensor relative to the target point to be defined.

It may be necessary to reposition the end or other location of the position sensor should the distance between sensor and target point seem too large or if it cannot be assured that tumor and sensor move in the same way in the body, i.e. not stationary relative to each other.

However, it is also possible to insert the position sensor by means of some other method into the body in the site of the location to be irradiated and to fix it in place there by suitable means such as e.g. using an endoscope advantageously connected to the position sensor so that it can be tracked from outside of the body whether the position sensor is located suitably in the site of the tissue to be irradiated or whether it may require shifting still further which, of course, may also be checked by means of the method as, for example, as described above.

It is likewise possible to combine the two methods just described for positioning the position sensor.

The position sensor may remain in the body for the full duration of treatment or, alternatively, may also be newly inserted and positioned, where necessary, for each treatment session.

Radiating the body tissue marked by the position sensor may be carried out e.g. so that a lung tissue, moving due to respiration, is only radiated when the signals of the position sensor indicate that, at this time, the tumor is in a defined site circumscribing the isocenter. If the tumor wanders outside of this site due to a respiratory movement, the radiation source is simply signaled OFF until the site to be irradiated is again within the permitted site. Radiation of this kind is also termed "gated radiotherapy " and may be precisely performed in particular using the method in accordance with the invention. It is likewise possible that the position of the site to be irradiated changes due to the body being shifted out of place to such an extent that the site is again in a permitted site circumscribing the isocenter.

The apparatus for radiating a body in accordance with the invention comprises the position sensor described, which may be inserted in the body. Also provided is a controllable means for moving a body which is controlled by a controller so that it can be determined from the position of the position sensor determined by the controlling means whether a volume to be irradiated is within the permitted or desired site e.g. circumscribing the isocenter or not. On the basis of the position of the volume to be irradiated, as determined from evaluation of the signals of the position sensor, the body, and thus the site to be irradiated, is positioned and, where necessary, the radiation source is switched ON/OFF depending on the position of the site to be irradiated as established at the time.

In this arrangement, the radiation source may be steered around a patient to be irradiated as known, the patient being thereby positioned preferably stationary on a movable device, i.e. e.g. on a table or a suitable bench.

Since-as mentioned above-there is the possibility of the volume to be irradiated in the patient being shifted out of place, the patient located stationary, e.g. on a bench, may be moved prior to or also during radiotherapy when the signals of the position sensor indicate that e.g. a tumor has wandered too far from the isocenter. This relocation may occur when certain events have taken place, e.g. if the patient has moved, or be continuous e.g. to adapt to movements of the tumor due to respiration. Suitably relocating the patient on the basis of the signals of the position sensor or adapting the angle of the bench or table may ensure the desired success of the treatment, it being just as possible, however, to suitably reposition or move the radiation source itself depending on the sensor signals e.g. by altering the gantry angle.

It is of advantage to use a flexible sensor as the position sensor, enabling the curvature and thus the precise location of its position, preferably the location of all points in space located on the sensor, to be detected on the basis of the output signals.

Preferably, an optical fiber, in particular a glass fiber sensor is used as the position sensor since this is very visible in a computer tomograph in relation to the circumscribing tissue and has no disadvantageous effect on the circumscribing tissue. Glass fiber cables are particularly suitable for insertion in the tissue due to their bio-compatibility.

Position sensors consisting of glass fibers are known in general and are based on different principles such as e.g. measuring a modulation of the light passing through as influenced by a curvature. Bragg gratings, for example, may be etched to the surface of a glass fiber cable to obtain information as to the curvature and, thus, the position of the glass fiber by measuring the light passing through or reflected by the glass fiber cable. It is also possible to group together an array of individual diffraction or position sensors and to use this array as a position sensor in accordance with the invention, whereby such position sensors may also be based on mechanical or other principles. Since such position sensors are known from prior art they are not detailed here.

Preferably, an incorporation aid is provided at the end of the position sensor to be inserted or at a defined distance away therefrom e.g. in the peripheral area of the position sensor, this placement aid consisting e.g. of an endoscope to recognize from outside of the patient's body whether the position sensor is located as desired. Supplementary thereto suitable means for curving the position sensor by control movements performed outside may be provided for e.g. steering the position sensor around a bone while being inserted in the body. For this purpose, various strips of plastics material or strips of some other material may be provided, for example, to produce a curvature in a desired direction by the shift in their relative position. In addition, it is also possible to apply specific fixing means to the position sensor such as e.g. elements extensible in various directions to anchor the position sensor stationary in a specific tissue.

Preferably, a connecting point is provided, e.g. on the controller or radiation device, as a fiducial point, the position of the connecting point being precisely defined three-dimensionally and, thus, also relative to the isocenter so that the precise three-dimensional location of the position sensor or individual desired points on the position sensor can be detected relative to the defined connecting point.

It is also possible to obtain a fiducial point for determining the three-dimensional location of the position sensor by applying one or more suitable markers to specifically defined positions of the position sensor which are not inserted in the body, which may be mapped by suitable sensor elements such as e.g. infrared cameras to thus define a three-dimensional fiducial point.

The present invention relates furthermore to the use of a position sensor, in particular an optical fiber for detecting the position of a site to be irradiated in a body.

BRIEF DESCRIPTION OF THE DRAWINGS

The invention will now be detailed by way of a preferred example embodiment with reference to the drawings in which:

FIG. 2   is an illustration of an embodiment of the position sensor in accordance with the invention.

DETAILED DESCRIPTION OF THE PREFERRED EMBODIMENT

Figure 1:
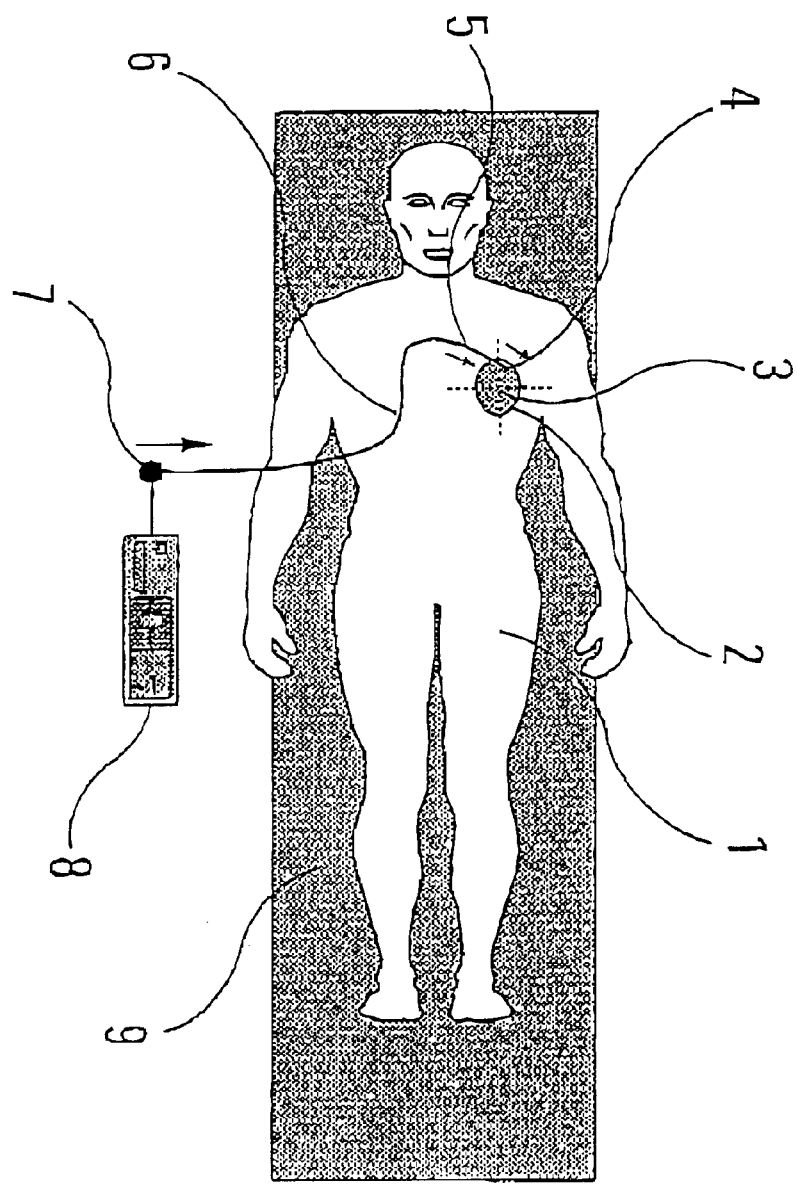
FIG. 1   is an illustration of a patient to be irradiated for a tumor and an inserted position sensor.

Referring now to FIG. 1, there is illustrated a patient 1 lying on a bench 9 of a radiation apparatus (not shown) with the tumor 2 to be irradiated. In the middle of the tumor a beam e.g. of a linear accelerator is focussed, termed isocenter. In this arrangement, it is required that the patient 1 is positioned so that the isocenter 3 is located in the center of the tumor 2 to be irradiated. A glass fiber cable 6, serving as the position sensor, is attached by its outer end 7 to a controller 8 so that the position and directional vector of the outgoing glass fiber cable 6 is clearly defined by a connecting point serving as a fiducial point to permit obtaining definite information as regards the location of a specific point or of several points, preferably as regards the location or curvature of the glass fiber 6 as a whole using this fiducial point. The other end of the glass fiber cable 6 is introduced into the body of the patient 1 and fixedly anchored in the site of the tumor 2, the end point 4 of the glass fiber cable 6 not being located in the isocenter 3. By using the positional information as regards the glass fiber cable 6 established by the controller 8, the absolute momentary position of the tumor 2 can be detected e.g. by determining the position of the end point 4 and/or of a further optional point 5 on the glass fiber cable, this also applying even when this tumor 2 moves e.g. due to respiration of the patient 1. Since e.g. the indicated points 4 and 5 of the glass fiber cable 6 are in a fixed location relative to the tumor 2, the momentary position of the tumor 2 may be detected despite a movement of the patient 1.

On the basis of the signals for detecting the position of individual points 4, 5 of the glass fiber cable 6, the controller 8 is able to determine whether the tumor 2 is just in the permitted site circumscribing the isocenter and to suitably control the patient bench 9 to position the tumor 2 and/or the radiation source accordingly. If the tumor 2 moves out of the isocenter 3, the radiation source can be switched OFF and only be turned ON again when the tumor 2 is again in the isocenter 3 due to a movement of the patient 1 or of the patient bench 9, this ON/OFF signaling procedure also being termed gating.

FIG. 2 illustrates an embodiment of the position sensor in accordance with the invention. Here, a glass fiber cable 6, serving as a position sensor, is surrounded by a sheath 10. Arranged within the sheath 10 surrounding the glass fiber cable 6, are one or more strips 11a, 11b of a plastics material or some other material so that, due to a strip 11a, 11b or the position of the strips 11a, 11b relative to one another being shifted from outside, the glass fiber cable 6 can be suitably curved, for example during insertion in the tissue, so as to steer the glass fiber cable 6 e.g. around a bone.

Arranged in the front end portion of the glass fiber cable 6 are one or more extensible elements 12 which can be shifted from a remote end of the glass fiber cable 6, as indicated by the arrow 13, so that these elements 12 can be extended from the sheath surface of the surrounding sheath after the glass fiber cable 6 has been inserted to anchor the glass fiber cable 6 in a tissue, to a bone or similar by means of the extensible elements 12.

To facilitate inserting the glass fiber cable 6, an endoscope 14 is provided in the front end portion so that, during the insertion process, it can be determined from outside of the body whether the glass fiber cable 6 is located in a desired tissue site.

Once the glass fiber cable 6 has been inserted, one or more of the optionally provided fiducial points 15 may be used to mark the precise location of the tumor to be irradiated by a defined position of the tumor relative to one or more of the fiducial points 15.

It is, of course, also possible to multiply provide or to totally eliminate some of the elements shown, such as e.g. the extensible element 12 or the endoscope 14, the position sensor used in each case permitting precise positioning of the site to be irradiated.

What is claimed is:
1. A method for positioning a body for radiation comprising:
   a) inserting a flexible position sensor into said body, the flexible position sensor including a plurality of fiducial points along a sensor length, wherein a curvature of the position sensor may be detected at a given point along the sensor length;
   b) detecting (i) a position of at least one fiducial point of the position sensor relative to a point or volume to be irradiated and (ii) the curvature of the position sensor adjacent the at least one fiducial point; and
   c) responsive to step b), positioning said body so that said point or volume to be irradiated is located in a specific site relative to an isocenter of an irradiation device.

2. The method as set forth in claim 1, wherein more than one fiducial point of said position sensor are made use of to define the location of said position sensor relative to said point or volume to be irradiated.

3. The method as set forth in claim 1, wherein step b) includes detecting a locational relationship of said sensor by determining a spacing and a direction of at least one fiducial point relative to the point or the volume to be irradiated.

4. The method as set forth in claim 1, wherein said position sensor is fixed in place relatively shift-proof in said body in relation to said point or volume to be irradiated.

5. The method as set forth in claim 1, wherein the detection of said location of said position sensor is performed using a computer tomograph or nuclear spin tomograph.

6. The method as set forth in claim 1, wherein step a) includes inserting said position sensor using an endoscopic technique.

7. The method as set forth in claim 1, wherein step c) includes shifting said body using a controllable bench.

8. The method as set forth in claim 1, further comprising interrupting radiation when the signals of said position sensor indicate that said location to be irradiated is outside of a defined site circumscribing said isocenter.

9. The method as set forth in claim 1, wherein a new positioning of said body occurs when said signals of said position sensor indicate that said point or volume to be irradiated is outside of the site circumscribing the isocenter.

10. The method as set forth in claim 1, wherein said signals of said position sensor are used to control a radiation source.

11. An apparatus for positioning a body including:
    a) a flexible position sensor, which can be placed into the body, said flexible position sensor including a plurality of fiducial points along a sensor length;
    b) at least one detector for detecting signals indicative of (i) a position of at least one fiducial point of the sensor relative to a point or volume to be irradiated and (ii) a curvature of the position sensor adjacent the at least one fiducial point;
    c) a controllable bench for moving the body; and
    d) a controller which controls the controllable bench for moving the body depending on the signals detected by the at least one detector.

12. The apparatus as set forth in claim 11, wherein the flexible position sensor is an optical fiber.

13. The apparatus as set forth in claim 12, wherein the optical fiber position sensor is a glass fiber.

14. The apparatus as set forth in claim 11, wherein the position sensor includes incorporation aids.

15. The apparatus as set forth in claim 11, wherein the at least one detector includes an optical system for sensing the position of a fiducial point of the position sensor.

16. The apparatus as set forth in claim 11, further comprising a radiation source which may be controlled depending on the signals sensed by the at least one detector.

17. The apparatus as set forth in claim 11, wherein the position sensor is an optical fiber for three-dimensionally detecting a position of a site to be irradiated in the body.

* * * * *